(12) United States Patent
Chu

(10) Patent No.: US 6,926,724 B1
(45) Date of Patent: Aug. 9, 2005

(54) VISCERAL ANASTOMOTIC DEVICE AND METHOD OF USING SAME

(75) Inventor: David Z. J. Chu, Pasadena, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/563,839

(22) Filed: May 4, 2000

Related U.S. Application Data

(60) Provisional application No. 60/132,692, filed on May 4, 1999.

(51) Int. Cl.[7] .............................................. A61B 17/08
(52) U.S. Cl. ....................... 606/155; 606/153; 606/154
(58) Field of Search ............................... 606/108, 153, 606/154, 155, 198, 194, 195; 623/4.2, 1.38, 623/1.15, 1.17, 1.2, 1.29, 1.32

(56) References Cited

U.S. PATENT DOCUMENTS

| | | | | |
|---|---|---|---|---|
| 1,470,707 A | * | 10/1923 | Bates | 606/154 |
| 3,155,095 A | * | 11/1964 | Brown | 606/154 |
| 3,683,926 A | * | 8/1972 | Suzuki | 606/154 |
| 4,190,909 A | * | 3/1980 | Ablaza | 623/1.32 |
| 4,313,231 A | * | 2/1982 | Koyamada | 623/1.32 |
| 4,769,029 A | * | 9/1988 | Patel | 606/155 |
| 5,141,516 A | | 8/1992 | Detweiler | |
| 5,180,392 A | * | 1/1993 | Skeie et al. | 606/155 |
| 5,476,506 A | * | 12/1995 | Lunn | 623/1.28 |
| 5,503,635 A | * | 4/1996 | Sauer et al. | 606/153 |
| 5,527,324 A | * | 6/1996 | Krantz et al. | 606/154 |
| 5,549,122 A | | 8/1996 | Detweilwer | |
| 5,607,464 A | * | 3/1997 | Trescony et al. | |
| 5,653,744 A | | 8/1997 | Khouri | |
| 5,725,547 A | * | 3/1998 | Chuter | 606/191 |
| 5,749,895 A | * | 5/1998 | Sawyer et al. | 606/214 |
| 5,800,524 A | * | 9/1998 | Borghi | 606/153 |
| 6,001,117 A | * | 12/1999 | Huxel et al. | 606/191 |
| 6,005,020 A | * | 12/1999 | Loomis | 424/401 |

* cited by examiner

Primary Examiner—Glenn K. Dawson
Assistant Examiner—Darwin P Erezo
(74) Attorney, Agent, or Firm—Rothwell Figg Ernst & Manbeck

(57) ABSTRACT

A temporary biocompatible stent and method for visceral anastomosis. The stent is provided with integral means for maintaining the structural stability of the stent while providing substantial flexibility. The method comprises fitting the luminal stumps of the viscus over either end of a stent of the invention, and joining the ends of each stump together. A short time after completion of the anastomosis, the stent dissolves and is absorbed safely into the body. The stent and method can be beneficially used in laparoscopic or more invasive traditional surgical procedures. The stent and method are particularly well suited for anastomosis of the bowel.

7 Claims, 1 Drawing Sheet

VISCERAL ANASTOMOTIC DEVICE AND METHOD OF USING SAME

CROSS REFERENCE TO RELATED APPLICATION

This application is related to provisional application Ser. No. 60/132,692, filed May 4, 1999, which is incorporated herein by reference.

BACKGROUND OF THE INVENTION

1. Field of the Invention

The procedure of choice to correct or relieve blocked or diseased luminal viscera of the body, such as the bowel, bile duct, ureter, and blood vessels in the medical field involves ligation and surgical anastomosis. Typically, a blocked or restricted luminal viscus, or a lesion or tumor on the viscus wall, is repaired whereby the abnormal portion is removed forming a break in the lumen. The break is then repaired by rejoining the two healthy luminal portions. Commonly, this was done by the surgeon with hand stitches or surgical staples. This procedure is performed on numerous tubular organs of the body, including the intestines and bowel, the bile duct, ureter, fallopian tubes, and blood vessels. These previous methods proved time consuming and required a great amount of skill and effort on the part of the surgeon. Additionally, this hand method is quite invasive as it cannot be satisfactorily done through laparoscopic techniques.

To simplify the task of reconnecting the severed lumens, known as anastomosis, there have been various attempts to utilize stents comprised of a biocompatible material inside the lumen to serve as a structure upon which to staple the two luminal stumps together. Such stents are typically of a general hollow cylindrical shape, and made from a rigid biocompatible material which will dissolve and absorb safely into the body after the anastomosis is complete.

2. Prior Art

U.S. Pat. No. 5,653,744 issued to Khouri relates to the use of such stent devices in the anastomosis of blood vessels. The stent is comprised of a material which is biocompatible and can be converted by heat into a liquid which is completely and safely miscible in blood.

U.S. Pat. Nos. 5,141,516 and 5,549,122, both issued to Detweiler, relate to a two-piece intraluminal stent for vessel anastomosis. The pieces are designed to interfit together such that a piece is placed inside the end of each vessel stump such that the stumps can be then locked together by joining the stent pieces. The vessel's stump ends are then permanently joined with a glue-like biocompatible sealant. The stent pieces are comprised of a dissolvable, biocompatible material, such as a crystallized saccharide, such that stent completely dissolves within several hours after anastomosis.

Additionally, attempts have been made in the art to utilize transient biocompatible stents comprised of polyglycolic acid, or "PGA," in the shape of rigid hollow cylinders. Schmidt, R. A., "Experimental Technique for (Laparoscopic) Bowel Anastomosis: Transient Enduluminally Stented Anastomosis (TESA)," Surgical Laparoscopy & Endoscopy, 7(4):281–284 (1997). The opposing vessel stumps are fit over the PGA stent and permanently joined using sutures or surgical staples. Also known is the BAR, or Biofragmentable Anastomotic Ring, which was used clinically very briefly, due to its awkwardness and difficulty in using.

The above mentioned attempts have been unsuccessful in providing an adequately simplified method for anastomosis. The above methods still require a great deal of effort in their use, and their designs make them quite restrictive when used in tight quarters such as during laparoscopic procedures. It is therefore an object of this invention to provide an improved method and device for mammalian anastomosis.

SUMMARY OF THE INVENTION

The invention relates to a method for mammalian anastomosis. More specifically, the invention relates to anastomosis of luminal viscera using an improved biocompatible and bio-absorbable stent.

The stent used in the present invention is comprised of a biocompatible material, such as polyglycolic acid ("PGA"), in the form of a semi-rigid tubular structure. Means are provided integral to the stent's construction whereby it is given flexibility without compromising its strength and therefore its ability to serve as an effective frame for anastomosis. Therefore, the surgeon is provided with a flexible stent which allows the luminal stumps to be more easily reconnected by the use of sutures, surgical staples, biocompatible sealants, or other known techniques. The advantages of such a stent are especially apparent when the anastomosis is performed by laparoscopic techniques.

A stent of the present invention, and the accompanying method of its use, can be employed in the anastomosis of various hollow organs including the intestines, bowel, bile duct, ureter, and fallopian tubes. The outside diameter and thickness of the stent can be varied such that it can provide sufficient structural strength and hold the stumps of the luminal viscus snugly in place without increasing the difficulty in manipulating the stent.

These and further aspects of the invention, as well as the following description of preferred embodiments of the invention, will best be understood when read in conjunction with reference to the figures. While the preferred embodiments of the invention are hereafter disclosed, it should be understood that the invention is not limited to the specific arrangements and instrumentalities described.

DETAILED DESCRIPTION OF THE INVENTION

Figure 1:
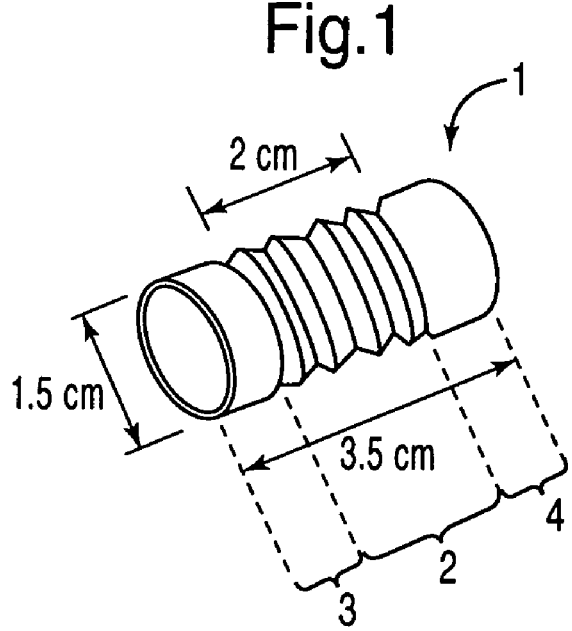
FIG. 1 is a side elevational view of one embodiment of the biocompatible stent according to the present invention.

Referring to the drawings, wherein like reference numerals indicate like elements throughout the several figures, there is depicted a biocompatible and dissolvable stent 1 of the present invention for use in the anastomosis of a mammalian luminal viscus 7. A particularly applicable use of the present invention is for anastomosis of the bowel.

A stent in accordance with the present invention is comprised of a biocompatible material which safely dissolves in the body after a short period of time. The material must have sufficient strength and lasting power to allow the surgeon enough time to complete the anastomosis, but preferably of a material that will also completely and safely dissolve into the body after a short period of time thereafter. Furthermore, the material must also be soft enough to allow easy penetration by sutures or surgical staples. A particularly suitable biocompatible material for use in the invention is comprised of PGA.

Figure 2:
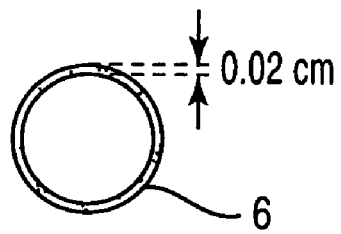
FIG. 2 is an axial cross-sectioned view of one embodiment of the biocompatible stent according to the present invention.

As made apparent by FIGS. 1 and 2, the stent preferably has a generally tubular or hollow cylindrical shape defined by the stent wall 6. This shape is advantageous because it provides a relatively large support surface upon which to rejoin the luminal stumps of the hollow viscus. This prevents the viscus from collapsing upon itself during reconnection. The anastomosis is more easily performed, and the repair remains intact while reducing risks of complications due to edema of the tissue. The stent's hollow structure allows it to lend support to the interior of the luminal viscus during surgery and for a short period afterward during healing. This interior support provided by the stent keeps the lumen from becoming blocked or restricted, thus allowing the organ to more quickly resume its normal functions. This in turn speeds the recovery of the patient.

Referring specifically to the embodiment depicted by FIG. 1, the stent 1 is comprised of three general sections, a flexible section 2 located between two smooth sections 3 and 4. The flexible section 2 contains means 5 integral to the stent' tubular wall 6 for providing flexibility to the stent without compromising the stent's strength against radial compression.

As shown in FIG. 1, an especially advantageous flexibility providing means 5 incorporates an accordion-like structure into the stent wall 6. Such a structure has circumferential crimping, such as that incorporated into the popularly known flexible drinking straw. Circumferential crimping has been found to be particularly advantageous because it allows a substantial amount of stent bending by the surgeon without compromising the strength of the stent wall 6. Additionally, this accordion-like structure also provides greater strength against compression than do non-crimped walls of like thickness. This therefore allows suitable stents having the accordion structure to be constructed with thinner walls than completely smooth stents. Such thinner stent walls can provide, if desirable for the particular medical application, a shortened time for the stent to completely dissolve into the body.

In the preferred embodiment of the stent, there is located at either terminal end of the stent 1, positioned on opposite ends of the flexible section, two smooth sections 3 and 4 of stent. These sections are substantially cylindrical in shape and are hollow along their axis, much like a pipe or tube. Both smooth sections are characterized in that they have smooth outer stent wall surfaces. This attribute is desirable because it allows ease in inserting the stent into the stump ends 7 of the luminal organ to be anastomosized. This feature is especially advantageous when the stent is to be used in laparoscopic procedures.

A stent of the present invention is made in various diameters, lengths, and wall thicknesses such that it can be adapted to the anastomosis of various anatomic viscera. The diameter of the stent is chosen such that the opposing ligated luminal stumps can pass over the ends of the stent without difficulty, yet still providing a snug fit. The length of the stent is likewise adapted to the particular anatomical vessel so as to provide a sufficient anchoring effect into each stump without making the stent so long as to hinder the ease of its manipulation. Similarly, the thickness of the stent wall can be varied according to different applications to provide sufficient support strength without unduly increasing the time it takes for the stent to completely dissolve.

By way of illustration, a stent according to the embodiment depicted in FIG. 1 which would be particularly suitable for use in the anastomosis of the bowel has a length of approximately 3.5 cm and an outside diameter of approximately 1.5 cm. Such a stent having a flexible section 2 comprised of circumferential crimping 5 of the stent wall 6 and made substantially of PGA would typically require a wall thickness of approximately 0.2 mm. The flexible section 2 would be approximately 2.0 cm long and located near the middle of the stent. The remaining 1.5 cm of length would have a smooth exterior surface. This remaining length would be broken up into two approximately even portions, smooth sections 3 and 4, on either end of the stent and on either side of the flexible section 2.

Stents of the present invention as described above would typically have a length to diameter ratio of approximately between 2:1 and 3:1. However, it should be understood to one of ordinary skill in the art that the ratios in the example above can and should be modified to customize the stent to the particular lumen size and type. Additionally, the smooth stent portions 3 and 4 can be constructed in various proportions with respect to the flexible portion 2 and toward one another (i.e., one being made longer than the other). Stents manufactured with equal length smooth sections 3 and 4 are preferred, however, because the symmetrical design is often less complicated to handle. If the situation arises where uneven length smooth sections are desired, the stents are sufficiently soft enough to be readily cut to the appropriate length by the physician.

Figure 3:
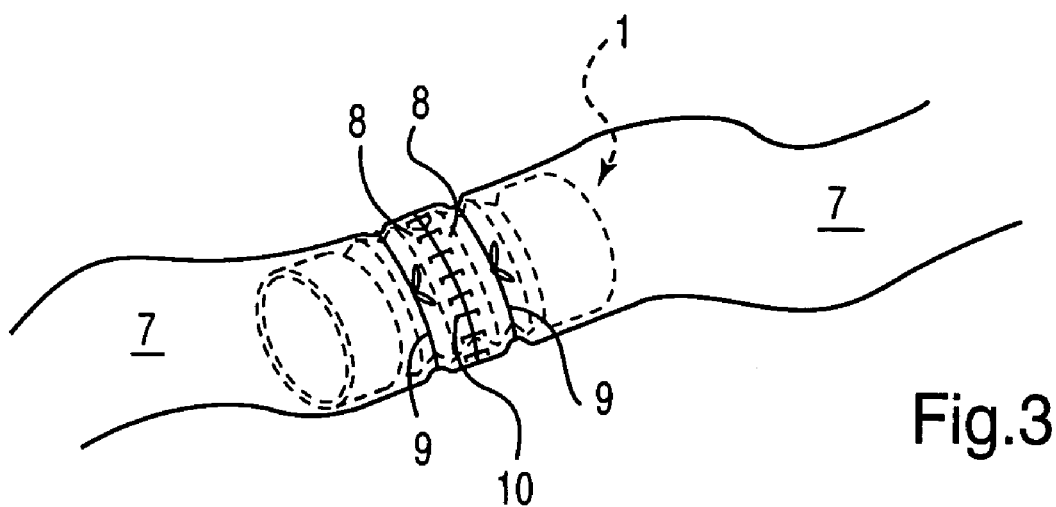
FIG. 3 is a side elevational view of one embodiment of the present invention showing a completed visceral anastomosis employing a biocompatible stent of the present invention.

The present invention also contemplates a method of mammalian visceral anastomosis using a flexible stent of the present invention. Such method may be readily adapted to both invasive and minimally invasive, such as laparoscopic, medical procedures. As shown in FIG. 3, after the surgeon has removed the unhealthy portion of the luminal viscus, one end of a stent of the present invention is inserted approximately halfway into one of the luminal stumps 7. This stump may then be secured in place by a circular suture tie over 9. Tying the first stump in place facilitates inserting the remaining exposed portion of the stent into the opposite stump without displacing the first stump. This process, especially in laparoscopic procedures, is made appreciably easier due to the flexibility of the stent.

When the stent used in the procedure has the circumferential crimping as in the preferred embodiment, the suture tie over should beneficially be made over a trough segment 8 of the crimping to more securely lock the first stump in place. If desired, the surgeon may also lock the second stump in place with a second suture tie. In these circumstances, the circumferential crimping has the additional benefit of providing a more secure anchoring of the stent into the stumps than would be possible with a smooth surfaced stent. This again reduces the difficulty of laparoscopic anastomoses.

Once the two opposing stump ends are touching and satisfactorily lined up with the aid of the stent, the stumps are then permanently secured together by the surgeon. Preferably, this is done with a series of surgical staples 10 placed circumferentially around the abutment of the two stumps with each staple spaced a small distance apart which varies from application to application. Alternatively, the surgeon may elect to use standard sutures, a biocompatible sealant, or other known means, but staples are preferred in most instances because of their ease of use in laparoscopic procedures.

The invention having thus been described, it will be apparent to those skilled in the art that the embodiments of the invention may be modified in many ways without departing from the spirit and scope of the invention. Therefore, any and all such modifications are intended to be included within the scope of the following claims.

What is claimed is:

1. A method of performing mammalian visceral anastomosis upon a luminal viscus ligated into two opposing stumps comprising the steps of:

inserting a stent having an elongated stent wall comprised substantially of a biocompatible material which dissolves after completion of anastomosis, wherein said stent wall forms a substantially tubular hollow structure, and wherein integral to said stent wall is means for providing bending flexibility to the stent wall without compromising the strength thereof, said means comprising a circumferential crimping of a portion of the stent wall, said stent wall having a length L, a distance approximately L/2 into the first stump of the ligated viscus such that a portion of the stent of length approximately L/2 remains extending outside the first stump;

inserting the remaining portion of the stent into the second stump whereby the two stumps are placed in a substantially abutting relationship; and joining the two luminal stumps together by surgical joining means.

2. The method according to claim 1, wherein the surgical joining means comprises a plurality of surgical staples stapling the two luminal stumps together circumferentially along their abutment.

3. The method according to claim 1, wherein the surgical joining means comprises a plurality of sutures for suturing the two luminal stumps together along their abutment.

4. The method according to claim 1, wherein the surgical joining means comprises a biocompatible surgical sealant for attaching the two luminal stumps together along their abutment.

5. The method according to claim 1, wherein the anastomosis is performed laparoscopically.

6. The method according to claim 1, wherein the method additionally comprises, after inserting the stent into the first luminal stump, the step of anchoring the stent into the first stump to prevent the stent from slipping while inserting the remaining portion of the stent into the second stump.

7. The method according to claim 1, wherein the luminal viscus is the bowel.

* * * * *